(12) United States Patent
Fukushima et al.

(10) Patent No.: US 6,576,794 B2
(45) Date of Patent: Jun. 10, 2003

(54) PROCESS FOR PRODUCTION OF ETHER AMINE

(75) Inventors: Tetsuaki Fukushima, Wakayama (JP); Hiroyuki Masuda, Wakayama (JP); Uichiro Nishimoto, Wakayama (JP); Hiroshi Abe, Barcelona (ES)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/015,657

(22) Filed: Dec. 17, 2001

(65) Prior Publication Data

US 2002/0158223 A1 Oct. 31, 2002

(30) Foreign Application Priority Data

Dec. 28, 2000 (JP) ......................................... 2000-403425

(51) Int. Cl.$^7$ ..................... C07C 253/30; C07C 209/48; C07C 209/26
(52) U.S. Cl. ........................ 564/292; 564/493; 568/697
(58) Field of Search ................................ 564/292, 493; 568/697

(56) References Cited

U.S. PATENT DOCUMENTS

| | | |
|---|---|---|
| 2,287,219 A | 6/1942 | Young, Jr. et al. |
| 2,372,624 A | 3/1945 | Carpenter |
| 5,874,625 A | 2/1999 | Elsasser |
| 6,114,585 A * | 9/2000 | Daly et al. .................. 564/505 |

FOREIGN PATENT DOCUMENTS

| | | |
|---|---|---|
| DE | 280 963 | 7/1990 |
| EP | 142 868 | 5/1985 |
| GB | 869 405 | 5/1961 |
| JP | 48-103505 | 12/1973 |

OTHER PUBLICATIONS

W.P. Utermohlen, Jr., "Preparation of γ–Alkoxy–n–propylamines", J. Am. Chem. Soc., vol. 67, 1945, pp. 1505–1506.
Derwent Publications, AN 1974–27833V, JP 48–103505, Dec. 12, 1973.

* cited by examiner

*Primary Examiner*—Brian Davis
(74) *Attorney, Agent, or Firm*—Oblon, Spivak, McClelland, Maier & Neustadt, P.C.

(57) ABSTRACT

A process for producing an ether amine (3), which comprises reacting a primary or secondary alcohol (1), ROH, with acrylonitrile in an amount of 0.8 to 1.2 equivalents of the alcohol (1) in the presence of an alkali metal hydroxide in an amount of not less than 0.01 part by weight, but less than 0.05 part by weight per 100 parts by weight of the alcohol (1) to obtain an alkyloxypropionitrile (2), and then adding water to the reaction system without removing the alkali metal hydroxide therefrom and effecting hydrogenation using a hydrogenation catalyst:

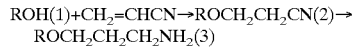

$$ROH(1) + CH_2=CHCN \rightarrow ROCH_2CH_2CN(2) \rightarrow ROCH_2CH_2CH_2NH_2(3)$$

wherein R denotes a linear or branched alkyl or alkenyl group having 6 to 24 carbon atoms. Also disclosed are a process for producing an ether tertiary amine (5), R—O—CH$_2$—CH$_2$—CH$_2$—N(CH$_2$R$^1$)$_2$, which comprises adding an aldehyde to the resulting ether amine (3) in the presence of a metal catalyst or a Raney nickel catalyst, and a process for producing an ether quaternary ammonium salt (6), R—O—CH$_2$—CH$_2$—CH$_2$—N(CH$_2$R$^1$)$_2$(R$^2$), which comprises reacting a quaternizing agent with the ether tertiary amine (5).

11 Claims, No Drawings

PROCESS FOR PRODUCTION OF ETHER AMINE

BACKGROUND OF THE INVENTION

1. Field of the Invention

The present invention relates to processes for producing an ether amine, an ether tertiary amine and an ether quaternary ammonium salt which are useful as softening agents, rinse bases or raw materials thereof, or raw materials for production of surfactants, dyes, acid gas removers, functional polymers, etc.

2. Description of the Prior Art

In a production process of an alkyloxypropylamine, an alkoxypropionitrile is at first prepared from an alcohol and acrylonitrile and then the product is hydrogenated. For example, the process by Uter Morene et al. [J. Am. Chem. Soc., Vol. 67, p. 1505 (1945)], the process described in British Patent No. 869,405 and the like are known. In these processes, however, a hydrogenation reaction is conducted under a high hydrogen pressure of about 100 kg/cm², and thus an expensive apparatus is required, and an operation for removing ammonia used in the process is essential. Therefore, these processes cannot be said to be industrially useful. On the other hand, Japanese Patent Application Laid-Open No. 103505/1973 discloses a process in which an alkali metal hydroxide is used to obtain a nitrile, and the resulting nitrile is hydrogenated under a hydrogen pressure of about 25 kg/cm² or lower after the alkali metal hydroxide is removed. This process requires a complicated operation for removing the alkali metal hydroxide, and its yield is low. So the process has not been satisfactory as a process for producing an alkyloxypropylamine through an alkyloxypropionitrile on an industrial scale.

SUMMARY OF THE INVENTION

It is an object of the present invention to provide a process for producing industrially advantageously an ether amine containing neither unreacted compounds nor by-products, having a high purity and scarcely colored, and processes for directly producing an ether tertiary amine and an ether quaternary ammonium salt from the ether amine thus obtained.

The present inventors have found that when the amount of the alkali metal hydroxide used in the step of cyanoethylating an alcohol is decreased to an amount less than that conventionally used, the purity of the alkyloxypropionitrile obtained as an intermediate is markedly increased, and the resulting reaction product can be subjected to a subsequent hydrogenation step without removing the alkali metal hydroxide therefrom to obtain an intended ether amine with a high purity and industrial advantages. The present inventors have also found that an ether tertiary amine and an ether quaternary ammonium salt each having a high purity can be efficiently produced from the ether amine thus obtained without need of any purification step.

According to the present invention, there is thus provided a process for producing an ether amine represented by the general formula (3):

wherein R denotes a linear or branched alkyl or alkenyl group having 6 to 24 carbon atoms, which comprises reacting a primary or secondary alcohol represented by the general formula (1):

wherein R has the same meaning as defined above, with an acrylonitrile in an amount of 0.8 to 1.2 equivalents relative to the amount of the alcohol (1) in the presence of an alkali metal hydroxide in an amount of not less than 0.01 part by weight but less than 0.05 part by weight per 100 parts by weight of the alcohol (cyanoethylation step) to give an alkyloxypropionitrile represented by the general formula (2):

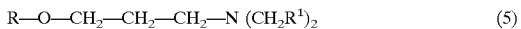

wherein R has the same meaning as defined above, and then adding water in an amount of 0.5 to 20 parts by weight per 100 parts by weight of the alkyloxy-propionitrile to the reaction system without removing the alkali metal hydroxide from the reaction system and effecting hydrogenation using a hydrogenation catalyst (hydrogenation step).

According to the present invention, there is also provided a process for producing an ether tertiary amine represented by the general formula (5):

wherein $R^1$ denotes hydrogen or a linear or branched alkyl group having 1 to 5 carbon atoms, and R has the same meaning as defined above, which comprises, subsequent to the above-described hydrogenation step, adding an aldehyde represented by the general formula (4):

$$R^1CHO \qquad (4)$$

wherein $R^1$ has the same meaning as defined above, to the ether amine represented by the general formula (3) defined above at a reaction temperature of 60 to 200° C. under a hydrogen pressure of at least 0.5 MPa (gauge pressure) in the presence of a metal catalyst containing at least one element selected from the group consisting of Pd, Pt, Rh, Re and Ru, or a Raney nickel catalyst (tertiary amine forming step).

According to the present invention, there is also provided a process for producing an ether quaternary ammonium salt represented by the general formula (6):

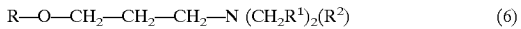

wherein $R^2$ denotes a linear or branched alkyl or hydroxyalkyl group having 1 to 5 carbon atoms, and R and $R^1$ have the same meanings as defined above, which comprises, subsequent to the above-described tertiary amine forming step, reacting the ether tertiary amine represented by the general formula (5) defined above with a quaternary salt forming agent (quaternary ammonium salt forming step).

According to the present invention, there can be produced industrially advantageously an ether amine containing neither unreacted compounds nor by-products, having a high purity and less colored. In addition, an ether tertiary amine and an ether quaternary ammonium salt each having a high purity can be efficiently produced from the ether amine thus obtained without need of any purification step.

DETAILED DESCRIPTION OF THE PREFERRED EMBODIMENTS

The process for production of an ether amine according to the present invention comprises a cyanoethylation step and a hydrogenation step.

Cyanoethylation Step

The cyanoethylation step is a step for producing an alkyloxypropionitrile (2) from a primary or secondary alcohol (1) and acrylonitrile.

Examples of the primary or secondary alcohol (1) include n-hexanol, 2-ethylhexanol, isodecanol, lauryl alcohol, tridecanol, palmityl alcohol, stearyl alcohol, isostearyl alcohol and 2-octyldodecanol. Among these, linear alcohols are preferred.

The amount of acrylonitrile to be used is 0.8 to 1.2 equivalents, preferably 0.9 to 1.2 equivalents, more preferably 0.95 to 1.1 equivalents relative to that of the alcohol (1). If the amount of acrylonitrile exceeds 1.2 equivalents, hydrogenation activity is lowered, thereby lowering selectivity. If the amount of acrylonitrile is less than 0.8 equivalent, unreacted alcohol remains to lower the yield.

Examples of the alkali metal hydroxide used in this step include lithium hydroxide, sodium hydroxide and potassium hydroxide, with potassium hydroxide and sodium hydroxide being particularly preferred from the viewpoint of reactivity. One or more of these alkali metal hydroxides can be used, and the amount thereof is not less than 0.01 part by weight, but less than 0.05 part by weight, and is preferably 0.01 to 0.04 part by weight per 100 parts by weight of the raw material alcohol (1) because unreacted acrylonitrile is decomposed or polymerized, or the resulting alkyloxypropionitrile is decomposed to lower the yield of the intended product if an higher amount of the alkali metal hydroxide relative to the raw material alcohol (1) is present.

The reaction temperature in this step is preferably 45 to 70° C., particularly preferably 50 to 65° C. The reaction time is preferably 0.5 to 5 hours.

Hydrogenation Step

The hydrogenating step is a step for obtaining the intended ether amine (3) by the hydrogenation reaction of the alkyloxypropionitrile (2).

In the present invention, the reaction product obtained in the above-described cyanoethylation step is used in the hydrogenation step without removing the alkali metal hydroxide from the reaction system. In this step, the reaction is conducted by adding water in an amount of 0.5 to 20 parts by weight, preferably 3 to 15 parts by weight per 100 parts by weight of the nitrile (2) to the reaction system from the viewpoint of improving the dispersibility of the catalyst to enhance the yield.

As the hydrogenation catalyst, used are well known hydrogenation reaction catalysts such as cobalt catalysts, nickel catalysts, copper catalysts, noble metal catalysts and the like. Preferably, Ni-, Co- and/or Ru-based catalysts, more preferably Raney type catalysts are used, which catalysts may further contain the other metals, for example, aluminum, zinc, silicon and the like which are present in a Raney alloy as extractable alloy components upon production of the Raney catalyst. The catalyst may further contain a commonly used promoter, for example, metals selected from the group consisting of Cr, Fe, Co, Mn, Ta, Mo and Ti. On the other hand, a completely solid catalyst or a supported solid catalyst, for example, a catalyst with Ni, Co, Ru or the like supported on $Al_2O_3$, $TiO_2$, $ZrO_2$, ZnO, $MgO/Al_2O_3$, diatomaceous earth or the like, may also be used. The amount of the hydrogenation catalyst is preferably 0.05 to 5 parts by weight, particularly preferably 0.1 to 3 parts by weight per 100 parts by weight of the nitrile (2).

This step is preferably conducted under a low hydrogen pressure or medium hydrogen pressure, for example, a hydrogen pressure of 0.3 to 10 MPa. No particular limitation is imposed on the reaction temperature. However, the reaction is preferably conducted at a temperature ranging from 50 to 250° C., particularly from 70 to 180° C. The reaction time is preferably about 2 to 15 hours. In many cases, the temperature is preferably raised continuously or stepwise during the hydrogenation.

In this step, an alkali metal hydroxide may also be used from the viewpoint of controlling formation of a bis (alkyloxypropyl)amine by a corresponding amine formation reaction. The amount of the alkyl metal hydroxide is preferably not more than 0.4 part by weight, particularly not more than 0.2 part by weight per 100 parts by weight of the nitrile (2). The alkali metal hydroxide is preferably dissolved in the water to be added in this step. Examples of the alkali metal hydroxide used in this step include lithium hydroxide, sodium hydroxide and potassium hydroxide, with potassium hydroxide and sodium hydroxide being particularly preferred from the viewpoint of reactivity.

The amine (3) thus obtained may be used as the raw material in the subsequent step as it is, or may be purified by distillation or the like.

Tertiary Amine Formation Step (3)→(5)

When an aldehyde and hydrogen are used as tertiary amine forming agents, an ether tertiary amine (5) can be produced by the so-called reduction-alkylation of alkoxypropylamine (3), such as a reduction-methylation reaction. Examples of the aldehyde include formaldehyde, and alkylaldehydes having 2 to 6 carbon atom in total, such as acetaldehyde, propanal, butanal, pentanal, hexanal and 2-methylpentanal. Among these, formaldehyde and acetaldehyde are preferred. As the formaldehyde, may be used an aqueous solution (formalin) or a polymerized product such as paraformaldehyde. The amount of the aldehyde used is preferably 1.0 to 1.5 molar times, particularly 1.0 to 1.2 molar times relative to the amount of the activated hydrogen atoms contained in the nitrogen in the amine (3).

The catalyst is preferably a metal catalyst containing at least one element selected from the group consisting of Pd, Pt, Rh, Re and Ru, particularly Pd. Powder of any of the above-described metals may be used as the metal catalyst. However, the metal is preferably supported on a carrier. The amount of the metal supported is preferably 0.01 to 20% by weight, particularly 0.1 to 10% by weight based on the total weight of the catalyst. As the catalyst, may be also used a Raney nickel catalyst acidified with an organic acid as described in Japanese Patent Application Laid-open No.16751/89 gazette. However, the above-described metal catalysts are preferably used from the viewpoint of easy separation of compound (5) from the reaction products. The amount of the metal catalyst varies depending on the kind of amine (3), reaction conditions, etc. However, it is generally used in an amount of 2 to 20,000 ppm, preferably 2 to 2,000 ppm, more preferably 5 to 500 ppm in term of the metal based on the weight of amine (3).

This step is usually conducted by feeding the aldehyde (4) to the reaction system charged with the amine (3) and the metal catalyst in hydrogen gas. The hydrogen pressure (gauge pressure) is preferably at least 0.5 MPa, particularly 1 to 10 MPa. The reaction temperature is preferably 60 to 200° C., particularly 110 to 180° C. Addition of the aldehyde to the reaction system may be either continuously or intermittently, and the rate of the addition is adapted to the reaction rate. However, the addition is preferably conducted continuously at a constant rate. The time of the addition substantially corresponds to the reaction time and is usually 1 to 10 hours. After completion of the feeding of the aldehyde, the reaction mixture is preferably aged for additional 10 to 60 minutes.

Various tertiary amines (5) can be obtained in such manner. The resulting tertiary amine (5) may be used as the raw material in the subsequent step as it is, or may be purified by distillation or the like.

Quaternary Ammonium Salt Formation Step (5)→(6)

As the quaternizing reaction of the ether tertiary amine (5), a general quaternizing process may be used. For example, an ether quaternary ammonium salt (6) can be obtained in accordance with a conventional method, for example, by using a quaternizing agent in an amount of 0.9 to 10 moles per 1 mole of an amine compound (5) and conducting a reaction at a temperature of from 50 to 140° C. for 0.1 to 20 hours using a solvent, if necessary. Examples of the quaternizing agent used herein include alkyl halides, hydroxyalkyl halides and dialkylsulfates having linear or branched alkyl group(s) of 1 to 6 carbon atoms. Examples of the alkyl halides include methyl chloride and ethyl chloride, examples of the hydroxyalkyl halides include hydroxyethyl chloride, and examples of the dialkylsulfates include dimethylsulfate and diethylsulfate. Examples of the solvent used in the quaternizing reaction include water, methanol, ethanol, 2-propanol, acetone and long-chain alcohols. Alternatively, quaternized product (6) may also be obtained by adding an alkylene oxide of 2 to 4 carbon atoms as a quaternarizing agent to an acid salt of the tertiary amine (5).

The ether type cationic surfactant (6) thus obtained may be used as it is as a formulation component in the present products, or may also be used after purification by an ordinary purifying means.

EXAMPLES

Examples 1 to 6 and Comparative Examples 1 to 7

An alcohol and an alkali metal hydroxide were placed in a flask and heated to 120° C. to conduct a dehydration operation in the reaction system for 1 hour. After completion of the dehydration, the reaction system was cooled to the intended reaction temperature (A), and acrylonitrile was then added dropwise (drop time: B). After completion of the drop-wise addition, agitation was conducted (aging time: C) at the same temperature to obtain each alkyloxypropionitrile.

After the alkyloxypropionitrile (in Examples 1 to 6 and Comparative Examples 1 to 4, each of the resultant reaction mixtures was used as it is, and in Comparative Examples 5 to 7, each of the resultant reaction mixtures was washed with water to remove the alkali metal hydroxide before use), a catalyst, water and an alkali metal hydroxide were placed in an autoclave, and the interior of the reaction system was purged with hydrogen, the reaction system was heated to a reaction temperature (D) and pressurized (E) with hydrogen. A reaction was conducted while retaining this pressure. The end point of the reaction was determined to be the time the amount of hydrogen absorbed became zero. Thereafter, aging was conducted for 30 minutes. After completion of the reaction, the reaction system was cooled to 80° C., and the catalyst was removed by filtration to obtain each intended ether amine (3).

The measurements of purities and hues of the resultant ether amines and the evaluation of their appearances were conducted in accordance with the following respective methods. The results are shown in Tables 1 to 4.

Purity

Measured by gas chromatography.

Column: Ultra 2 (manufactured by Hewlett-Packard Co.), 25 m.

Detector: FID detector (detection temperature: 300° C.).

Measuring conditions:
  Kept at 60° C. for 2 minutes, and heated to 300° C. at a heating rate of 8° C./min;
  Inlet temperature: 300° C.;
  Flow rate of hydrogen: 80 ml/min (carrier gas: helium).

Hue

Measured by a Lovibond tintometer.

Appearance

⊚:Not turbid;

○:Slightly turbid;

x: Turbid.

TABLE 1

| | Example | | | |
|---|---|---|---|---|
| | 1 | 2 | 3 | 4 |
| Cyanoethylating step Raw Material | | | | |
| Raw alcohol | Stearyl alcohol [1] | Lauryl alcohol [2] | Lauryl alcohol [2] | Stearyl alcohol [1] |
| Charged amount of raw alcohol | 270 g (1.00 mol) | 188 g (1.00 mol) | 188 g (1.00 mol) | 270 g (1.00 mol) |
| Charged amount of acrylonitrile | 51 g (0.95 mol) | 58 g (1.10 mol) | 64 g (1.20 mol) | 56 g (1.06 mol) |
| Alkali metal hydroxide | Potassium hydroxide | Potassium hydroxide | Sodium hydroxide | Potassium hydroxide |
| Charged amount of alkali metal hydroxide | 0.04 g (0.01 parts by weight [a]) | 0.08 g (0.01 parts by weight [a]) | 0.03 g (0.01 parts by weight [a]) | 0.04 g (0.01 parts by weight [a]) |
| Reaction temperature (A) | 60° C. | 65° C. | 50° C. | 60° C. |
| Drop time (B) | 1.0 hour | 1.0 hour | 2.0 hours | 1.0 hour |
| Aging time (C) | 2.0 hours | 1.0 hour | 2.0 hours | 2.0 hours |
| Purity | 93.8% by weight | 96.9% by weight | 98.8% by weight | 97.8% by weight |
| Hydrogenation step Raw Material | | | | |
| Charged amount of nitrile [b] | 300 g | 300 g | 300 g | 300 g |

TABLE 1-continued

|  | Example | | | |
|---|---|---|---|---|
|  | 1 | 2 | 3 | 4 |
| Charged amount of water | 30.0 g | 9.0 g | 45.0 g | 30.0 g |
| Alkali metal hydroxide | Sodium hydroxide | Sodium hydroxide | Lithium hydroxide | Not used |
| Charged amount of alkali metal hydroxide *c | 0.3 g (0.10 parts by weight) | 1.2 g (0.40 parts by weight) | 0.3 g (0.10 parts by weight) | 0.0 g (0.00 parts by weight) |
| Hydrogenation catalyst | Raney type Ni—Al *5 | Raney type Ni—Mo—Al *6 | Raney type Co—Al *7 | Raney type Ni—Al *5 |
| Amount of catalyst *d | 3.6 g (0.60 parts by weight) | 3.0 g (1.00 parts by weight) | 6.0 g (2.00 parts by weight) | 6.0 g (2.00 parts by weight) |
| Reaction temperature (D) | 120° C. | 70° C. | 150° C. | 120° C. |
| Hydrogen pressure (E) | 2.0 MPa | 1.0 MPa | 1.5 MPa | 2.0 MPa |
| Purity of the intended product | 89.1% by weight | 94.2% by weight | 92.8% by weight | 93.2% by weight |
| Appearance | ⊙ | ⊙ | ⊙ | ⊙ |
| Hue APHA | 35 | 25 | 60 | 35 |

TABLE 2

|  | Example | |
|---|---|---|
|  | 5 | 6 |
| Cyanoethylating step Raw material |  |  |
| Raw alcohol | Isodecanol *1 | 2-Octyldodecanol *2 |
| Charged amount of raw alcohol | 160 g (1.00 mol) | 269 g (1.00 mol) |
| Charged amount of acrylonitrile | 56 g (1.06 mol) | 59 g (1.10 mol) |
| Alkali metal hydroxide | Potassium hydroxide | Sodium hydroxide |
| Charged amount of alkali metal hydroxide | 0.04 g (0.03 parts by weight *a) | 0.05 g (0.02 parts by weight *a) |
| Reaction temperature (A) | 60° C. | 65° C. |
| Drop time (B) | 1.0 hour | 1.0 hour |
| Aging time (C) | 2.0 hours | 2.0 hours |
| Purity | 94.8% by weight | 93.7% by weight |
| Hydrogenation step Raw material |  |  |
| Charged amount of nitrile *b | 300 g | 300 g |
| Charged amount of water | 25.0 g | 3.0 g |
| Alkali metal hydroxide | Sodium hydroxide | Potassium hydroxide |
| Charged amount of alkali metal hydroxide *c | 0.45 g (0.15 parts by weight) | 0.45 g (0.15 parts by weight) |
| Hydrogenation catalyst | Ni-diatomaceous earth *8 | Ru-carbon *9 |
| Amount of catalyst *d | 9.0 g (3.00 parts by weight) | 7.5 g (2.50 parts by weight) |
| Reaction temperature (D) | 180° C. | 140° C. |
| Hydrogen pressure (E) | 2.0 MPa | 2.0 MPa |
| Purity of the intended product | 91.9% by weight | 89.2% by weight |
| Appearance | ◯ | ◯ |
| Hue APHA | 70 | 85 |

TABLE 3

|  | Comparative Example | | | |
|---|---|---|---|---|
|  | 1 | 2 | 3 | 4 |
| Cyanoethylating step Raw material |  |  |  |  |
| Raw alcohol | Stearyl alcohol *1 | Lauryl alcohol *2 | Lauryl alcohol *2 | Stearyl alcohol *1 |
| Charged amount of raw acohol | 270 g (1.00 mol) | 188 g (1.00 mol) | 188 g (1.00 mol) | 270 g (1.00 mol) |
| Charged amount of acrylonitrile | 64 g (1.21 mol) | 58 g (1.10 mol) | 64 g (1.20 mol) | 56 g (1.06 mol) |
| Alkali metal hydroxide | Potassium hydroxide | Potassium hydroxide | Sodium hydroxide | Potassium hydroxide |
| Charged amount of alkali metal hydroxide | 0.14 g (0.05 parts by weight *a) | 0.14 g (0.07 parts by weight *a) | 0.03 g (0.02 parts by weight *a) | 0.18 g (0.07 parts by weight *a) |
| Reaction temperature (A) | 60° C. | 65° C. | 50° C. | 60° C. |
| Drop time (B) | 1.0 hour | 1.0 hour | 2.0 hours | 1.0 hour |
| Aging time (C) | 2.0 hours | 1.0 hour | 2.0 hours | 2.0 hours |
| Purity | 88.9% by weight | 91.2% by weight | 98.8% by weight | 89.2% by weight |
| Hydrogenation step |  |  |  |  |

TABLE 3-continued

| | Comparative Example | | | |
|---|---|---|---|---|
| | 1 | 2 | 3 | 4 |
| Raw material | | | | |
| Charged amount of nitrile *b | 300 g | 300 g | 300 g | 300 g |
| Charged amount of water | 30.0 g | 9.0 g | 62.0 g | 30.0 g |
| Alkali metal hydroxide | Sodium hydroxide | Sodium hydroxide | Lithium hydroxide | Not used |
| Charged amount of alkali metal hydroxide *c | 0.3 g (0.10 parts by weight) | 1.2 g (0.40 parts by weight) | 0.3 g (0.10 parts by weight) | 0.0 g (0.00 parts by weight) |
| Hydrogenation catalyst | Raney type Ni—Al *5 | Raney type Ni—Mo—Al *6 | Raney type Co—Al *7 | Raney type Ni—Al *5 |
| Amount of catalyst *d | 3.6 g (0.60 parts by weight) | 3.0 g (1.00 parts by weight) | 6.0 g (2.00 parts by weight) | 10.0 g (3.33 parts by weight) |
| Reaction temperature (D) | 120° C. | 70° C. | 150° C. | 120° C. |
| Hydrogen pressure (E) | 2.0 MPa | 1.0 MPa | 1.5 MPa | 2.0 MPa |
| Purity of the intended product | 79.8% by weight | 85.7% by weight | 79.8% by weight | 71.2% by weight |
| Appearance | X | X | X | X |
| Hue APHA | 10 | 120 | 90 | 95 |

TABLE 4

| | Comparative Example | | |
|---|---|---|---|
| | 5 | 6 | 7 |
| Cyanoethylating step | | | |
| Raw material | | | |
| Raw alcohol | Stearyl alcohol *1 | Lauryl alcohol *2 | Lauryl alcohol *2 |
| Charged amount of raw alcohol | 270 g (1.00 mol) | 188 g (1.00 mol) | 188 g (1.00 mol) |
| Charged amount of acrylonitrile | 64 g (1.21 mol) | 58 g (1.10 mol) | 64 g (1.20 mol) |
| Alkali metal hydroxide | Potassium hydroxide | Potassium hydroxide | Sodium hydroxide |
| Charged amount of alkali metal hydroxide | 2.00 g (0.74 parts by weight *a) | 1.50 g (0.80 parts by weight *a) | 0.03 g (0.02 parts by weight *a) |
| Reaction temperature (A) | 60° C. | 55° C. | 50° C. |
| Drop time (B) | 1.0 hour | 1.0 hour | 2.0 hours |
| Aging time (C) | 2.0 hours | 2.0 hours | 2.0 hours |
| Purity (after completion of reaction) | 81.5% by weight | 80.9% by weight | 83.8% by weight |
| Purity (after water washing) | 89.5% by weight | 88.7% by weight | 89.7% by weight |
| Hydrogenation step | | | |
| Raw material | | | |
| Charged amount of nitrile *b | 300 g | 300 g | 300 g |
| Charged amount of water | 30.0 g | 9.0 g | 0.0 g |
| Alkali metal hydroxide | Sodium hydroxide | Not used | Not used |
| Charged amount of alkali metal hydroxide *c | 2.5 g (0.40 parts by weight) | 0.0 g (0.00 part by weight) | 0.0 g (0.00 part by weight) |
| Hydrogenation catalyst | Raney type Ni—Mo—Al *6 | Raney type Ni—Mo—Al *6 | Ni-diatomaceous earth *8 |
| Amount of catalyst *d | 3.6 g (0.60 parts by weight) | 3.0 g (1.00 parts by weight) | 6.0 g (2.00 parts by weight) |
| Reaction temperature (D) | 120° C. | 150° C. | 180° C. |
| Hydrogen pressure (E) | 1.0 MPa | 1.0 MPa | 1.5 MPa |
| Purity of the intended product | 72.6% by weight | 68.9% by weight | Reaction was not completed |
| Appearance | X | X | X |
| Hue APHA | 200 | 180 | — |

*1: Kalcohol 8098, product of Kao Corporation (hydroxyl value: 207)
*2: Kalcohol 2098, product of Kao Corporation (hydroxyl value: 299)
*3: Product of Kyowa Hakko Kogyo Co., Ltd. hydroxyl value: 352)
*4: Kalcohol 200GD, product of Kao Corporation (hydroxyl value: 189)
*5: B-113W, product of Degussa-Huls AG (water content: 50%)
*6: R-239, product of Nikko Rica Corporation (water content: 50%)
*7: R-400, product of Nikko Rica Corporation (water content: 50%)
*8: Flake Ni, product of Sakai Chemical Industry Co., Ltd.
*9: Ru/C, product of NE Chemcat Co. (water content: 50%)
*a: Per 100 parts by weight of the raw alcohol
*b: As a reaction mixture (product) of the cyanoethylating step
*c: As an amount added in the hydrogenating step (per 100 parts by weight of the reaction mixture of the cyanoethylation)
*d: As an amount of a pure catalyst (per 100 parts by weight of the reaction mixture of the cyanoethylation)

Example 1A

A 2-L autoclave was charged with octadecyloxypropylamine (300 g) obtained in Example 1 and a 5% Pd/C catalyst (product of NE Chemcat Co., water content: 50%, 0.6 g) and purged with hydrogen. After the reaction system was heated to 120° C., formalin (2.1 moles) was continuously fed over 5 hours while stirring the contents and pressurizing the reaction system to 2.0 MPa with hydrogen at a discharge flow rate (flow rate at the outlet of the autoclave) of 5 L/h. At this time, hydrogen was fed so as to retain the hydrogen pressure of 2.0 MPa, since hydrogen was absorbed by a reaction. After feeding formalin, aging was conducted for 30 minutes to complete the reaction. After cooling, the reaction slurry was taken out and filtered (using 5C filter paper). When the filtrate was left at rest, it was separated into 2 layers. An upper layer (oil layer) was taken out and washed several times with a 48% aqueous solution of sodium hydroxide. Remaining low-boiling substances such as water and formaldehyde were removed under reduced pressure, and the residue was analyzed by gas chromatography (hereafter abbreviated as "GC"). As a result, it was found that the amine reacted quantitatively, and the intended N,N-dimethyl-3-octadecyloxypropylamine was obtained at a purity of 88.8% (GC area %).

Example 2A

A 2-L autoclave was charged with dodecyloxypropylamine (300 g) obtained in Example 2 and a 20% Pd/alumina catalyst (product of NE Chemcat Co., 0.75 g) and purged with hydrogen. After the reaction system was heated to 130° C., acetaldehyde (2.1 moles) was continuously fed over 10 hours while stirring the contents and pressurizing the reaction system to 2.0 MPa with hydrogen at a discharge flow rate (flow rate at the outlet of the autoclave) of 0 L/h. At this time, hydrogen was fed so as to retain the hydrogen pressure of 2.0 MPa, since hydrogen was absorbed by a reaction. After feeding acetaldehyde, aging was conducted for 30 minutes to complete the reaction. After cooling, the reaction slurry was taken out and filtered (using 5C filter paper). The filtrate was left at rest to conduct phase separation and take out an upper layer (oil layer). Remaining low-boiling substances such as water and acetaldehyde were removed under reduced pressure, and the residue was analyzed by GC. As a result, it was found that the whole amine reacted, and the intended N,N-diethyl-3-dodecyloxypropylamine was obtained at a purity of 90.8% (GC area %).

Example 3A

A 2-L autoclave was charged with dodecyloxypropylamine (300 g) obtained in Example 3, a 5% Pd/alumina catalyst (product of NE Chemcat Co., 12 g) and water (50 g), and purged with hydrogen. After the reaction system was heated to 110° C., formalin (2.2 moles) was continuously fed over 6 hours while stirring the contents and pressurizing the reaction system to 10.0 MPa with hydrogen at a discharge flow rate (flow rate at the outlet of the autoclave) of 10 L/h. At this time, hydrogen was fed so as to retain the hydrogen pressure of 10.0 MPa, since hydrogen was absorbed by a reaction. After feeding formalin, aging was conducted for 60 minutes to complete the reaction. After cooling, the reaction slurry was taken out and filtered (using 5C filter paper). Flake of caustic soda (5 moles to excessive formalin) was charged into the filtrate, and the mixture was stirred at 80° C. for 1 hour. After the mixture was left at rest to conduct phase separation, a lower layer (water layer) was taken out, and an upper layer (oil layer) was washed with water (300 g×2 times). Remaining low-boiling substances such as water were removed under reduced pressure, and the residue was analyzed by GC. As a result, it was found that the whole amine reacted, and the intended N,N-dimethyl-3-dodecyloxypropylamine was obtained at a purity of 90.8% (GC area %).

Example 4A

A 2-L autoclave was charged with octadecyloxypropylamine (300 g) obtained in Example 4, Raney nickel (product of Nikko Rica Corporation, water content: 50%, 6 g) and water (100 g), and purged with hydrogen. After the reaction system was heated to 150° C., formalin (2.1 moles) was continuously fed over 4 hours while stirring the contents and pressurizing the reaction system to 0.5 MPa with hydrogen at a discharge flow rate (flow rate at the outlet of the autoclave) of 5 L/h. At this time, hydrogen was fed so as to retain the hydrogen pressure of 0.5 MPa, since hydrogen was absorbed by a reaction. After feeding formalin, aging was conducted for 30 minutes to complete the reaction. After cooling, the reaction slurry was taken out and filtered (using 5C filter paper). Flake of caustic soda (5 moles to excessive formalin) was charged into the filtrate, and the mixture was stirred at 80° C. for 1 hour. After the mixture was left at rest to conduct phase separation, a lower layer (water layer) was taken out, and an upper layer (oil layer) was washed with water (300 g×2 times). Remaining low-boiling substances such as water, methanol and formaldehyde were removed under reduced pressure, and the residue was analyzed by GC. As a result, it was found that the whole amine reacted, and the intended N,N-dimethyl-3-octadecyloxypropylamine was obtained at a purity of 87.2% (GC area %).

Example 5A

A 2-L autoclave was charged with N-isodecyloxypropylamine (300 g) obtained in Example 5 and a 10% Pd/silica catalyst (product of NE Chemcat Co., 3 g) and purged with hydrogen. After the reaction system was heated to 130° C., acetaldehyde (2.1 moles) was continuously fed over 4 hours while stirring the contents and pressurizing the reaction system to 2.0 MPa with hydrogen at a discharge flow rate (flow rate at the outlet of the autoclave) of 5 L/h. At this time, hydrogen was fed so as to retain the hydrogen pressure of 2.0 MPa, since hydrogen was absorbed by a reaction. After feeding acetaldehyde, aging was conducted for 30 minutes to complete the reaction. After cooling, the reaction slurry was taken out and filtered (using 5C filter paper). The filtrate was left at rest to conduct phase separation and take out a transparent upper layer (oil layer). The upper layer was washed several times with a 48% aqueous solution of sodium hydroxide. Remaining low-boiling substances such as water, methanol and acetaldehyde were removed under reduced pressure, and the residue was analyzed by GC. As a result, it was found that the whole amine reacted, and the intended N,N-diethyl-3-isodecyloxypropylamine was obtained at a purity of 85.8% (GC area %).

Example 6A

A 2-L autoclave was charged with 2-octyldodecyloxypropylamine (300 g) obtained in Example 6, a 5% Pd/C catalyst (product of NE Chemcat Co., water content: 50%, 6 g) and water (5 g), and purged with hydrogen. After the reaction system was heated to 120° C., formalin (2.1 moles) was continuously fed over 5 hours while stirring the contents and pressurizing the reaction system to 0.5 MPa with hydrogen at a discharge flow rate (flow rate at the outlet of the autoclave) of 5 L/h. At this time, hydrogen was fed so as to retain the hydrogen pressure of 0.5 MPa, since hydrogen was absorbed by a reaction. After feeding formalin, aging was conducted for 30 minutes to complete the reaction. After cooling, the reaction slurry was taken out and filtered (using 5C filter paper). The filtrate was left at rest to conduct phase separation and take out a transparent upper layer (oil layer). Remaining low-boiling substances such as a water and acetaldehyde were removed under reduced pressure, and the residue was analyzed by GC. As a result, it was found that the whole amine reacted, and the intended N,N-dimethyl-[3-(2-octyl)dodecyloxypropyl]-amine was obtained at a purity of 88.1% (GC area %).

Comparative Example 1A

An operation was conducted in the same manner as in Example 1A except that octadecyloxypropylamine obtained in Comparative Example 1 was used as an alkyloxypropylamine, thereby obtaining the intended N,N-dimethyl-3-octadecyloxy-propylamine. The purity thereof was 78.8% (GC area %), and the oil layer was turbid.

Comparative Example 2A

An operation was conducted in the same manner as in Example 2A except that dodecyloxypropylamine obtained in Comparative Example 2 was used as an alkyloxypropylamine, thereby obtaining the intended N,N-diethyl-3-dodecyloxypropylamine.

The purity thereof was 70.1% (GC area %), and the oil layer was turbid.

Comparative Example 3A

An operation was conducted in the same manner as in Example 1A except that the amount of the 5% Pd/C catalyst (product of NE Chemcat Co., water content: 50%) used was changed to 0.012 g, and the resultant oil layer was analyzed by GC. As a result, it was found that the raw amine remained unreacted.

Example 1B

A 1-L autoclave equipped with a stirrer and a thermometer was charged with N,N-dimethyl-3-octadecyloxypropylamine (300 g) obtained in Example 1A, isopropyl alcohol (90 g) and methyl chloride (100 g) to conduct a reaction at 90° C. for 6 hours. Excessive methyl chloride was topped to obtain an isopropyl alcohol solution of N,N,N-trimethyl-3-octadecyloxypropylammonium chloride. The quaternizing rate was 98% (KSTM 20082).

What is claimed is:

1. A process for producing an ether amine represented by the general formula (3):

ROCH$_2$CH$_2$CH$_2$NH$_2$  (3)

wherein R denotes a linear or branched alkyl or alkenyl group having 6 to 24 carbon atoms, which comprises reacting a primary or secondary alcohol represented by the general formula (1):

ROH  (1)

wherein R has the same meaning as defined above, with acrylonitrile in an amount of 0.8 to 1.2 equivalents of the alcohol (1) in the presence of an alkali metal hydroxide in an amount of not less than 0.01 part by weight, but less than 0.05 part by weight per 100 parts by weight of the alcohol (1) to obtain an alkyloxypropionitrile represented by the general formula (2):

ROCH$_2$CH$_2$CN  (2)

wherein R has the same meaning as defined above, and then adding water in an amount of 0.5 to 20 parts by weight per 100 parts by weight of the alkyloxypropionitrile to the reaction system without removing the alkali metal hydroxide from the reaction system and effecting hydrogenation using a hydrogenation catalyst.

2. The process according to claim 1, wherein the alkali metal hydroxide is selected from the group consisting of lithium hydroxide, sodium hydroxide and potassium hydroxide.

3. A process for producing an ether tertiary amine represented by the general formula (5):

R—O—CH$_2$—CH$_2$—CH$_2$—N (CH$_2$R$^1$)$_2$  (5)

wherein R denotes a linear or branched alkyl or alkenyl group having 6 to 24 carbon atoms and R$^1$ denotes hydrogen or a linear or branched alkyl group having 1 to 5 carbon atoms, which comprises, subsequent to the process according to claim 1, adding an aldehyde represented by the general formula (4):

R$^1$CHO  (4)

wherein R$^1$ has the same meaning as defined above, to the ether amine represented by the general formula (3):

ROCH$_2$CH$_2$CH$_2$NH$_2$  (3)

wherein R has the same meaning as defined above, at a reaction temperature of from 60 to 200° C. under a hydrogen pressure of at least 0.5 MPa (gauge pressure) in the presence of a metal catalyst containing at least one element selected from the group consisting of Pd, Pt, Rh, Re and Ru or a Raney nickel catalyst.

4. A process for producing an ether quaternary ammonium salt represented by the general formula (6):

R—O—CH$_2$—CH$_2$—CH$_2$—N(CH$_2$R$^1$)$_2$(R$^2$)  (6)

wherein R denotes a linear or branched alkyl or alkenyl group having 6 to 24 carbon atoms, R$^1$ denotes hydrogen or a linear or branched alkyl group having 1 to 5 carbon atoms and R$^2$ denotes a linear or branched alkyl or hydroxyalkyl group having 1 to 5 carbon atoms, which comprises, subsequent to the process according to claim 3, reacting a quaternizing agent with the ether tertiary amine represented by the general formula (5):

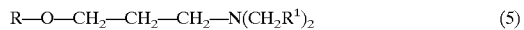

R—O—CH$_2$—CH$_2$—CH$_2$—N(CH$_2$R$^1$)$_2$  (5)

wherein R and R$^1$ have the same meanings as defined above.

5. The process according to claim 1, wherein the amount of alkali metal hydroxide is 0.01 to 0.04 part by weight per 100 parts by weight of the alcohol (1).

6. The process according to claim 1, wherein the alkali metal hydroxide is sodium hydroxide.

7. The process according to claim 1, wherein the alkali metal hydroxide is lithium hydroxide.

8. The process according to claim 1, wherein the alcohol (1) is lauryl alcohol.

9. The process according to claim 1, wherein the alcohol (1) is stearyl alcohol.

10. The process according to claim 1, wherein the alcohol (1) is isodecanol.

11. The process according to claim 1, wherein the alcohol (1) is 2-octyldodecanol.

* * * * *